(12) United States Patent
Kovtun et al.

(10) Patent No.: US 9,579,064 B2
(45) Date of Patent: Feb. 28, 2017

(54) MEDICAL DEVICES FOR MAPPING CARDIAC TISSUE

(71) Applicant: BOSTON SCIENTIFIC SCIMED, INC., Maple Grove, MN (US)

(72) Inventors: Vladimir V. Kovtun, Inver Grove Heights, MN (US); Carlos Alberto Ricci, Apple Valley, MN (US); Pramodsingh Hirasingh Thakur, Woodbury, MN (US); Shibaji Shome, Arden Hills, MN (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 0 days.

(21) Appl. No.: 14/717,684

(22) Filed: May 20, 2015

(65) Prior Publication Data

US 2015/0342536 A1 Dec. 3, 2015

Related U.S. Application Data

(60) Provisional application No. 62/007,310, filed on Jun. 3, 2014.

(51) Int. Cl.
*A61B 5/04* (2006.01)
*A61B 5/00* (2006.01)
(Continued)

(52) U.S. Cl.
CPC ........... *A61B 5/7214* (2013.01); *A61B 5/0245* (2013.01); *A61B 5/04012* (2013.01);
(Continued)

(58) Field of Classification Search
CPC . A61B 5/0245; A61B 5/04012; A61B 5/0422; A61B 5/6858; A61B 5/7203; A61B 5/7214
See application file for complete search history.

(56) References Cited

U.S. PATENT DOCUMENTS 4,407,296 A 10/1983 Anderson
4,962,767 A 10/1990 Brownlee
(Continued)

FOREIGN PATENT DOCUMENTS

CN 1253761 A 5/2000
CN 200960161 Y 10/2007
(Continued)

OTHER PUBLICATIONS

International Preliminary Report on Patentability issued in PCT/US2013/076958, mailed Jun. 30, 2015, 8 pages.
(Continued)

*Primary Examiner* — George Manuel
(74) *Attorney, Agent, or Firm* — Faegre Baker Daniels LLP

(57) ABSTRACT

Medical devices and methods for making and using medical devices are disclosed. A method for removing an artifact of a biological reference signal present in a biological source signal may comprise sensing a biological reference signal with one or more electrodes and sensing a biological source signal, wherein the biological source signal comprises an artifact of the biological reference signal. The method may further comprise determining, based on the biological reference signal, the artifact of the biological reference signal and subtracting the artifact of the biological reference signal from the sensed biological source signal.

20 Claims, 12 Drawing Sheets

(51) Int. Cl.
*A61B 5/0245* (2006.01)
*A61B 5/042* (2006.01)
(52) U.S. Cl.
CPC .......... *A61B 5/0422* (2013.01); *A61B 5/6858* (2013.01); *A61B 5/7203* (2013.01)

(56) References Cited

U.S. PATENT DOCUMENTS

| | | | |
|---|---|---|---|
| 5,161,539 | A | 11/1992 | Evans et al. |
| 5,647,870 | A | 7/1997 | Kordis et al. |
| 5,683,425 | A | 11/1997 | Hauptmann |
| 5,772,693 | A | 6/1998 | Brownlee |
| 5,776,072 | A | 7/1998 | Hsu et al. |
| 5,782,898 | A | 7/1998 | Dahl et al. |
| 5,817,133 | A | 10/1998 | Houben |
| 6,070,094 | A | 5/2000 | Swanson et al. |
| 6,214,025 | B1 | 4/2001 | Thistle et al. |
| 6,233,491 | B1 | 5/2001 | Kordis et al. |
| 6,236,383 | B1 | 5/2001 | Nakajima et al. |
| 6,650,931 | B1 | 11/2003 | McClure et al. |
| 6,660,021 | B1 | 12/2003 | Palmer et al. |
| 6,735,465 | B2 | 5/2004 | Panescu |
| 6,810,283 | B2 | 10/2004 | Suribhotla et al. |
| 7,338,512 | B2 | 3/2008 | McGuckin, Jr. et al. |
| 7,672,722 | B1 | 3/2010 | Mengotto |
| 7,780,694 | B2 | 8/2010 | Palmer et al. |
| 7,850,708 | B2 | 12/2010 | Pal |
| 7,933,643 | B1 | 4/2011 | Gill et al. |
| 8,019,409 | B2 | 9/2011 | Rosenberg et al. |
| 8,055,333 | B2 * | 11/2011 | Duann et al. ............. 600/516 |
| 8,060,202 | B2 | 11/2011 | Betzold et al. |
| 8,090,434 | B2 | 1/2012 | Lian et al. |
| 8,155,739 | B2 | 4/2012 | Keel et al. |
| 8,165,666 | B1 | 4/2012 | Briggs et al. |
| 8,175,693 | B2 | 5/2012 | Rosenberg et al. |
| 8,195,292 | B2 | 6/2012 | Rosenberg et al. |
| 8,543,195 | B1 | 9/2013 | Brockway et al. |
| 9,131,866 | B2 | 9/2015 | Thakur et al. |
| 9,439,578 | B2 | 9/2016 | Thakur et al. |
| 2003/0236466 | A1 | 12/2003 | Tarjan et al. |
| 2004/0176694 | A1 | 9/2004 | Kim et al. |
| 2005/0154321 | A1 | 7/2005 | Wolinsky et al. |
| 2005/0209678 | A1 | 9/2005 | Henkes et al. |
| 2005/0288600 | A1 | 12/2005 | Zhang et al. |
| 2006/0069322 | A1 | 3/2006 | Zhang et al. |
| 2006/0116595 | A1 | 6/2006 | Palreddy et al. |
| 2006/0253044 | A1 | 11/2006 | Zhang et al. |
| 2008/0194979 | A1 | 8/2008 | Madry et al. |
| 2008/0243214 | A1 | 10/2008 | Koblish |
| 2008/0281369 | A1 | 11/2008 | KenKnight et al. |
| 2009/0240157 | A1 | 9/2009 | Lian et al. |
| 2009/0254140 | A1 | 10/2009 | Rosenberg et al. |
| 2009/0306732 | A1 | 12/2009 | Rosenberg et al. |
| 2009/0318995 | A1 | 12/2009 | Keel et al. |
| 2010/0152801 | A1 | 6/2010 | Koh et al. |
| 2010/0256699 | A1 * | 10/2010 | Makdissi ..................... 607/5 |
| 2010/0268059 | A1 | 10/2010 | Ryu et al. |
| 2011/0054559 | A1 | 3/2011 | Rosenberg et al. |
| 2011/0054560 | A1 | 3/2011 | Rosenberg et al. |
| 2011/0066201 | A1 | 3/2011 | Rosenberg et al. |
| 2011/0066202 | A1 | 3/2011 | Rosenberg et al. |
| 2011/0066203 | A1 | 3/2011 | Rosenberg et al. |
| 2011/0092809 | A1 | 4/2011 | Nguyen et al. |
| 2011/0118803 | A1 | 5/2011 | Hou et al. |
| 2011/0144510 | A1 | 6/2011 | Ryu et al. |
| 2011/0184274 | A1 | 7/2011 | Rosenberg et al. |
| 2011/0213260 | A1 | 9/2011 | Keel et al. |
| 2011/0251505 | A1 | 10/2011 | Narayan et al. |
| 2011/0295137 | A1 | 12/2011 | Rosenberg et al. |
| 2011/0319954 | A1 | 12/2011 | Niazi et al. |
| 2012/0157865 | A1 | 6/2012 | Stein et al. |
| 2012/0184863 | A1 | 7/2012 | Harlev et al. |
| 2012/0327204 | A1 | 12/2012 | Friedman et al. |
| 2013/0274582 | A1 | 10/2013 | Afonso et al. |
| 2013/0345537 | A1 | 12/2013 | Thakur et al. |
| 2013/0345577 | A1 | 12/2013 | Thakur et al. |
| 2013/0345583 | A1 | 12/2013 | Thakur et al. |
| 2014/0018792 | A1 | 1/2014 | Gang et al. |
| 2014/0067279 | A1 | 3/2014 | George et al. |
| 2014/0187991 | A1 * | 7/2014 | Thakur et al. ............... 600/521 |
| 2014/0316294 | A1 | 10/2014 | Maskara et al. |
| 2015/0257671 | A1 | 9/2015 | Laughner et al. |
| 2015/0342536 | A1 | 12/2015 | Kovtun et al. |
| 2016/0345853 | A1 | 12/2016 | Thakur et al. |

FOREIGN PATENT DOCUMENTS

| | | |
|---|---|---|
| CN | 101365379 A | 2/2009 |
| CN | 101558993 A | 10/2009 |
| EP | 1543865 A1 | 6/2005 |
| EP | 2863792 A1 | 4/2015 |
| EP | 2863793 A1 | 4/2015 |
| JP | H11511666 A | 10/1999 |
| JP | 2005501674 A | 1/2005 |
| JP | 2006025836 A | 2/2006 |
| JP | 2013523344 A | 6/2013 |
| JP | 2014502556 A | 2/2014 |
| WO | WO0045700 A1 | 8/2000 |
| WO | WO0047278 A1 | 8/2000 |
| WO | WO03022356 A2 | 3/2003 |
| WO | WO2006037172 A1 | 4/2006 |
| WO | WO2008118992 A1 | 10/2008 |
| WO | WO2011041489 A2 | 4/2011 |
| WO | WO2011075328 A1 | 6/2011 |
| WO | 2014058484 A1 | 4/2014 |
| WO | 2015187371 A1 | 12/2015 |

OTHER PUBLICATIONS

International Search Report and Written Opinion issued in International Application No. PCT/US2013/046843, mailed Oct. 23, 2013, 12 pages.
International Search Report and Written Opinion issued in PCT/US2013/046841, mailed Oct. 15, 2013, 12 pages.
International Search Report and Written Opinion issued in PCT/US2013/076958, mailed Apr. 7, 2014, 14 pages.
International Search Report and Written Opinion issued in PCT/US2015/031787, mailed Aug. 5, 2015, 11 pages.
Potter, M. et al., "Competing ICA Techniques in Biomedical Signal Analysis", Electrical and Computer Engineering, 2001, Canadian Conference on May 13-16, 2001, Piscataway, NJ, USA, IEEE, vol. 2, May 13, 2001, pp. 987-992.
Zhou, Yu et al., "A New United Analysis Method for Epicardial Mapping Signals", Bioinformatics and Biomedical Engineering, 2008, ICBBE 2008, the Second International Conference, IEEE, Piscataway, NJ, USA, May 16, 2008, pp. 636-639.

* cited by examiner

MEDICAL DEVICES FOR MAPPING CARDIAC TISSUE

CROSS-REFERENCE TO RELATED APPLICATIONS

This application claims priority under 35 U.S.C. §119 to U.S. Provisional Application Ser. No. 62/007,310, filed Jun. 3, 2014, the entirety of which is incorporated herein by reference.

TECHNICAL FIELD

The present disclosure pertains to medical devices and systems. More particularly, the present disclosure pertains to medical devices and methods for mapping and/or ablating cardiac tissue.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure describes medical devices, systems, and methods for mapping and/or ablating cardiac tissue. In a first example, a catheter system for mapping a chamber of a heart, the system comprising: a first plurality of electrodes configured to sense a biological reference signal; a second plurality of electrodes configured to sense a biological source signal, wherein the biological source signal comprises an artifact of the biological reference signal; a processor connected to the second plurality of electrodes, wherein the processor is configured to: determine, based on the biological reference signal, the artifact of the biological reference signal; and subtract the artifact of the biological reference signal from the sensed biological source signal.

Alternatively or additionally to the examples above, in another example, to determine, based on the biological reference signal, the artifact of the biological reference signal, the processor is configured to compensate for differences between the biological reference signal and the artifact of the biological reference signal.

Alternatively or additionally to the examples above, in another example, to compensate for differences between the biological reference signal and the artifact of the biological reference signal, the processor is configured to generate one or more shifted copies of the biological reference signal.

Alternatively or additionally to the examples above, in another example, to compensate for differences between the biological reference signal and the artifact of the biological reference signal, the processor is further configured to: generate, based at least in part on the generated one or more shifted copies of the biological reference signal, an estimated artifact of the biological reference signal.

Alternatively or additionally to the examples above, in another example, to subtract the artifact of the biological reference signal from the sensed biological source signal, the processor is configured to subtract the estimated artifact of the biological reference signal from the sensed biological source signal.

Alternatively or additionally to the examples above, in another example, to generate, based at least in part on the generated one or more shifted copies of the biological reference signal, an estimated artifact of the biological reference signal, the processor is configured to: form a projection matrix comprising the biological reference signal and one or more shifted copies of the biological reference signal; determining a set of linear combination coefficients using a projection technique; and form the estimated artifact of the biological reference signal from the projection matrix and the set of linear combination coefficients.

Alternatively or additionally to the examples above, in another example, the projection technique comprises of or more of: least-squares regression; constrained least-squares; maximum likelihood estimation; non-linear programming; and linear programming.

Alternatively or additionally to the examples above, in another example, to generate, based at least in part on the generated one or more shifted copies of the biological reference signal, an estimated artifact of the biological reference signal, the processor is configured to: generate a convolution matrix H comprising the biological reference signal and one or more shifted copies of the biological reference signal; and determine an optimal multiplication vector x, such that a product of the convolution matrix H and the optimal multiplication vector x produce a solution vector b', where the solution vector b' is a solution that is most closely correlated to the biological source signal.

Alternatively or additionally to the examples above, in another example, the processor is further configured to reduce redundancy in the biological reference signal.

Alternatively or additionally to the examples above, in another example, the processor is further configured to identify beat timings in the biological reference signal.

Alternatively or additionally to the examples above, in another example, the processor is further configured to: identify beat windows around the identified beat timings in the biological reference signal and the biological source signal; and concatenate the beat windows to produce a concatenated biological reference signal and a concatenated biological source signal.

Alternatively or additionally to the examples above, in another example, the biological reference signal is a far-field signal and the biological source signal is a near-field signal.

Alternatively or additionally to the examples above, in another example, the biological reference signal is a ventricular cardiac signal and the biological source signal is an atrial cardiac signal.

Alternatively or additionally to the examples above, in another example, the first plurality of electrodes comprise surface electrodes.

In another example, a method for removing an artifact of a biological reference signal present in a biological source signal comprises: sensing a biological reference signal with one or more electrodes; sensing a biological source signal, wherein the biological source signal comprises an artifact of the biological reference signal; determining, based on the biological reference signal, the artifact of the biological reference signal; and subtracting the artifact of the biological reference signal from the sensed biological source signal.

Alternatively or additionally to the examples above, in another example, determining, based on the biological reference signal, the artifact of the biological reference signal comprises compensating for differences between the biological reference signal and the artifact of the biological reference signal.

Alternatively or additionally to the examples above, in another example, compensating for differences between the biological reference signal and the artifact of the biological reference signal comprises generating one or more shifted copies of the biological reference signal.

Alternatively or additionally to the examples above, in another example, compensating for differences between the biological reference signal and the artifact of the biological reference signal comprises: generating, based at least in part on the generated one or more shifted copies of the biological reference signal, an estimated artifact of the biological reference signal.

Alternatively or additionally to the examples above, in another example, subtracting the artifact of the biological reference signal from the sensed biological source signal comprises subtracting the estimated artifact of the biological reference signal from the sensed biological source signal.

Alternatively or additionally to the examples above, in another example, generating, based at least in part on the generated one or more shifted copies of the biological reference signal, an estimated artifact of the biological reference signal comprises: forming a projection matrix comprising the biological reference signal and one or more shifted copies of the biological reference signal; determining a set of linear combination coefficients using a projection technique; and forming the estimated artifact of the biological reference signal from the projection matrix and the set of linear combination coefficients.

Alternatively or additionally to the examples above, in another example, the projection technique comprises one or more of: least-squares regression; constrained least-squares; maximum likelihood estimation; non-linear programming; and linear programming.

Alternatively or additionally to the examples above, in another example, generating, based at least in part on the generated one or more shifted copies of the biological reference signal, an estimated artifact of the biological reference signal comprises: generating a convolution matrix H comprising the biological reference signal and one or more shifted copies of the biological reference signal; and determining an optimal multiplication vector x, such that a product of the convolution matrix H and the optimal multiplication vector x produce a solution vector b', where the solution vector b' is a solution that is most closely correlated to the biological source signal.

Alternatively or additionally to the examples above, in another example, the method further comprises reducing redundancy in the biological reference signal.

Alternatively or additionally to the examples above, in another example, reducing the redundancy in the biological reference signal comprises performing principal component analysis on the biological reference signal.

Alternatively or additionally to the examples above, in another example, the method further comprises identifying beat timings in the biological reference signal.

Alternatively or additionally to the examples above, in another example, the method further comprises: identifying beat windows around the identified beat timings in the biological reference signal and the biological source signal; and concatenating the beat windows to produce a concatenated biological reference signal and a concatenated biological source signal.

In still another example, a catheter system for mapping a chamber of a heart comprises: a plurality of electrodes configured to sense a first set of one or more activation signals in the chamber of the heart, wherein each of the activation signals of the first set comprises a near-field signal component and a far-field signal component; one or more electrodes configured to sense a second set of one or more activation signals, wherein the second set of activation signals are representative of the far-field signal components of the first set of activation signals; and a processor configured to receive the sensed first set of one or more activation signals and the sensed second set of one or more second activation signals, wherein the processor is configured to: process the second set of activation signals; generate, based at least in part on the processed second set of activation signals, an estimated far-field signal component for each activation signal in the first set of activation signals; and subtract the estimated far-field signal components from the corresponding first activation signals.

Alternatively or additionally to the examples above, in another example, to generate, based at least in part on the processed second set of activation signals, an estimated far-field signal component for each activation signal in the first set of activation signals, the processor is configured to: generate one or more shifted copies of the processed second set of activation signals; project the one or more shifted copies onto each of the activation signals of first set of activation signals.

Alternatively or additionally to the examples above, in another example, projecting the one or more shifted copies onto each of the activation signals of the first set of activation signals produces the estimated far-field signal component for each activation signal in the first set of activation signals, wherein the estimated far-field signal components are the estimated far-field signal components that are most closely correlated to the far-field signal components of the activation signals in the first set of activation signals.

Alternatively or additionally to the examples above, in another example, projecting comprises performing one or more techniques comprised of: least-squares regression; constrained least-squares; maximum likelihood estimation; non-linear programming; and linear programming.

Alternatively or additionally to the examples above, in another example, to process the second set of activation signals, the processor is configured to: produce one or more concatenated beat window signals from the one or more second activation signals.

In still another example, a method for reducing a ventricular signal artifact in a sensed atrial signal comprises: sensing one or more ventricular signals with a plurality of electrodes; sensing an atrial signal using a plurality of electrodes, wherein the atrial signal comprises an atrial signal component and an artifact signal component that is representative of the one or more ventricular signals; and filtering, based at least in part on the sensed one or more ventricular signals, the atrial signal to reduce the artifact signal component, wherein the filtering accounts for differences between the one or more ventricular signals and the artifact signal component.

Alternatively or additionally to the examples above, in another example, filtering, based at least in part on the sensed one or more ventricular signals, the atrial signal to reduce the artifact signal component, comprises: generating one or more shifted copies of the one or more ventricular signals; generating, based at least in part on the generated one or more shifted copies of the one or more ventricular signals, an estimated artifact signal; and subtracting the estimated artifact signal from the atrial signal.

Alternatively or additionally to the examples above, in another example, generating, based at least in part on the generated one or more shifted copies of the one or more ventricular signals, an estimated artifact signal comprises back projecting the generated one or more shifted copies of the one or more ventricular signals onto the atrial signal.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
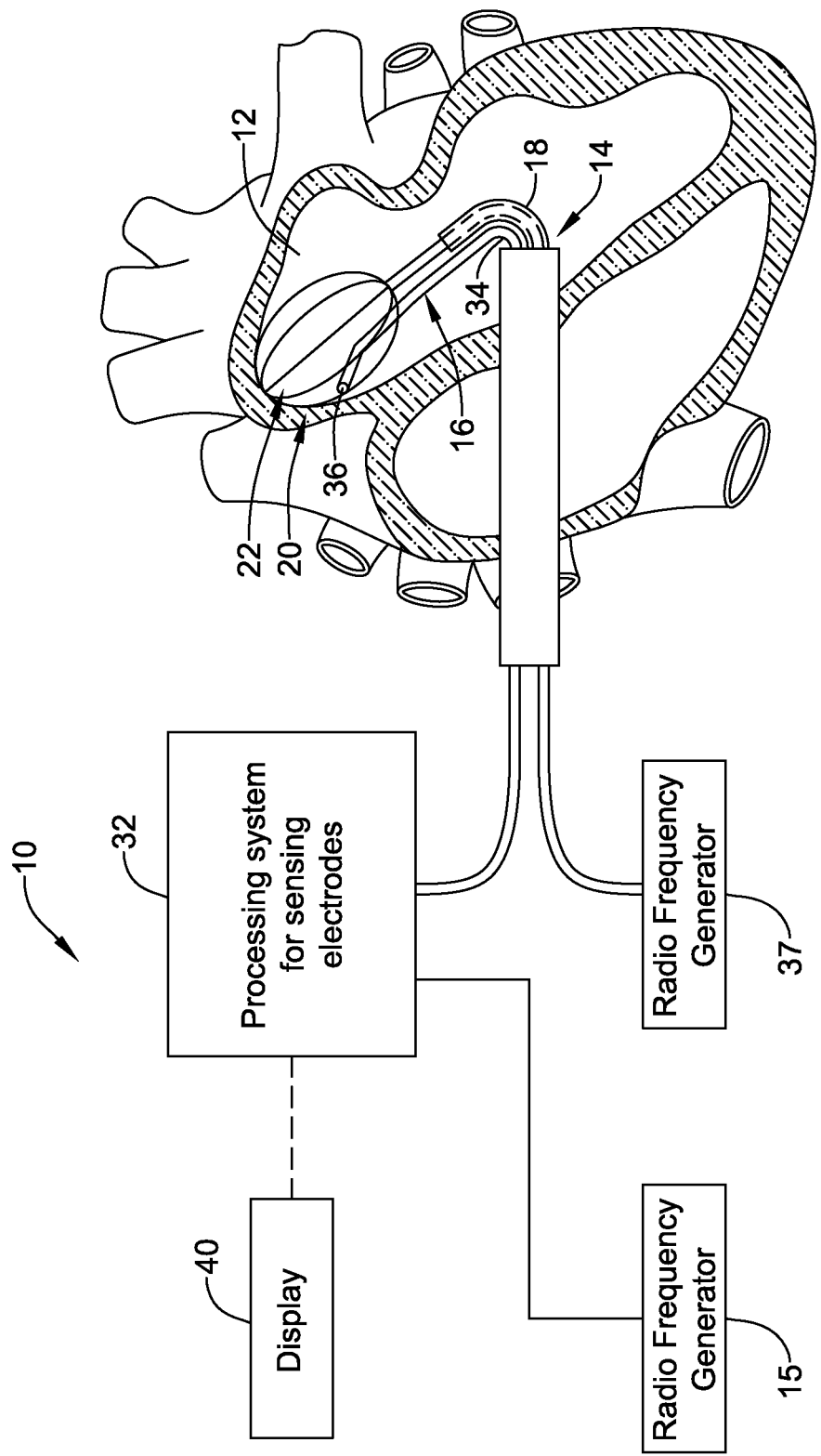
FIG. 1 is a schematic view of an example catheter system for accessing a targeted tissue region in the body for diagnostic and therapeutic purposes, in accordance with aspects of this disclosure.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an example", "some examples", "other examples", etc., indicate that the example described may include one or more particular features, structures, and/or characteristics. However, such recitations do not necessarily mean that all examples include the particular features, structures, and/or characteristics. Additionally, when particular features, structures, and/or characteristics are described in connection with one example, it should be understood that such features, structures, and/or characteristics may also be used connection with other examples whether or not explicitly described unless clearly stated to the contrary. Also, when particular features, structures, and/or characteristics are described in connection with one example, it is implicit that other examples may include less than all of the disclosed features, structures, and/or characteristics in all combinations.

The following detailed description should be read with reference to the drawings in which similar elements in different drawings are numbered the same. The drawings, which are not necessarily to scale, depict illustrative embodiments and are not intended to limit the scope of the invention.

Mapping the electrophysiology of heart rhythm disorders often involves the introduction of a constellation catheter or other mapping/sensing device having a plurality of electrodes and/or sensors (e.g., CONSTELLATION®, commercially available from Boston Scientific) into a cardiac chamber. The sensors, for example electrodes, detect cardiac electrical activity at sensor locations. It may be desirable to have the cardiac electrical activity processed into electrogram signals that accurately represent cellular excitation through cardiac tissue relative to the sensor locations. A processing system may then analyze and output the signal to a display device. Further, the processing system may output the signal as an activation or vector field map. A user, such as a physician, may use the activation or vector field map to perform a diagnostic procedure.

Some example catheters may include sixty-four or more electrodes which each detect cardiac electrical activity. Such electrodes may sense cardiac electrical activity that originates near the electrodes, e.g. near field signals, and cardiac electrical activity that originates away from the electrodes, e.g. far-field signals. In some cases, the electrodes may sense activity from both locations at similar times, such that the sensed signal is a combination of signals from each source. This disclosure describes various medical devices and techniques for modifying sensed electrical signals.

FIG. 1 is a schematic view of a system 10 for accessing a targeted tissue region in the body for diagnostic and/or therapeutic purposes. FIG. 1 generally shows the system 10 deployed in the left atrium of the heart. Alternatively, system 10 can be deployed in other regions of the heart, such as the left ventricle, right atrium, or right ventricle. While the illustrated embodiment shows system 10 being used for ablating myocardial tissue, system 10 (and the techniques described herein) may alternatively be configured for use in other tissue ablation applications, such as procedures for ablating tissue in the prostrate, brain, gall bladder, uterus, nerves, blood vessels and other regions of the body, including in systems that are not necessarily catheter-based.

System 10 includes mapping probe 14 and ablation probe 16. Each probe 14/16 may be separately introduced into the selected heart region 12 through a vein or artery (e.g., the femoral vein or artery) using a suitable percutaneous access technique. Alternatively, mapping probe 14 and ablation probe 16 can be assembled in an integrated structure for simultaneous introduction and deployment in the heart region 12.

Mapping probe 14 may include flexible catheter body 18. The distal end of catheter body 18 carries three-dimensional multiple electrode structure 20. In the illustrated embodiment, structure 20 takes the form of a basket defining an open interior space 22 (see FIG. 2), although other multiple electrode structures could be used. Structure 20 carries a plurality of mapping electrodes 24 (not explicitly shown on FIG. 1, but shown on FIG. 2) each having an electrode location on structure 20 and a conductive member. Each electrode 24 may be configured to sense or detect intrinsic physiological activity in an anatomical region adjacent to each electrode 24.

In some examples, electrodes 24 may be configured to detect activation signals of the intrinsic physiological activity within the anatomical structure. For example, intrinsic cardiac electrical activity may comprise repeating or semi-repeating waves of electrical activity with relatively large spikes in activity at the beginning of activation events. Electrodes 24 may sense such activation events and the times at which such activation events occur. Generally, electrodes 24 may sense activation events at different times as an electrical activity wave propagates through the heart. For instance, an electrical wave may begin near a first group of electrodes 24, which may sense an activation event at relatively the same time or within a relatively small window of time. As the electrical wave propagates through the heart, a second group of electrodes 24 may sense the activation even of the electrical wave at times later than the first group of electrodes 24.

Electrodes 24 are electrically coupled to processing system 32. A signal wire (not shown) may be electrically coupled to each electrode 24 on structure 20. The signal wires may extend through body 18 of probe 14 and electrically couple each electrode 24 to an input of processing system 32. Electrodes 24 sense cardiac electrical activity in the anatomical region, e.g., myocardial tissue, adjacent to their physical location within the heart. The sensed cardiac electrical activity (e.g., electrical signals generated by the heart which may include activation signals) may be processed by processing system 32 to assist a user, for example a physician, by generating an anatomical map (e.g., a vector field map, an activation time map) to identify one or more sites within the heart appropriate for a diagnostic and/or treatment procedure, such as an ablation procedure. For example, processing system 32 may identify a near-field signal component (e.g., activation signals originating from cellular tissue adjacent to mapping electrodes 24) or an obstructive far-field signal component (e.g., activation signals originating from non-adjacent tissue). In such examples where structure 20 is disposed in an atrium of the heart, as in FIG. 1, the near-field signal component may include activation signals originating from atrial myocardial tissue whereas the far-field signal component may include activation signals originating from ventricular myocardial tissue. In some instances, a user may only be interested in the near-field signal component, and system 10 may be configured to process the sensed signals to remove the sensed far-field signal component. The near-field activation signal component may then be further analyzed to find the presence of a pathology and to determine a location suitable for ablation for treatment of the pathology (e.g., ablation therapy).

Processing system 32 may include dedicated circuitry (e.g., discrete logic elements and one or more microcontrollers; application-specific integrated circuits (ASICs); or specially configured programmable devices, such as, for example, programmable logic devices (PLDs) or field programmable gate arrays (FPGAs)) for receiving and/or processing the acquired cardiac electrical activity. In some examples, processing system 32 includes a general purpose microprocessor and/or a specialized microprocessor (e.g., a digital signal processor, or DSP, which may be optimized for processing activation signals) that executes instructions to receive, analyze and display information associated with the received cardiac electrical activity. In such examples, processing system 32 can include program instructions, which when executed, perform part of the signal processing. Program instructions can include, for example, firmware, microcode or application code that is executed by microprocessors or microcontrollers. The above-mentioned implementations are merely exemplary, and the reader will appreciate that processing system 32 can take any suitable form for receiving electrical signals and processing the received electrical signals.

In some examples, processing system 32 may be configured to measure the sensed cardiac electrical activity in the myocardial tissue adjacent to electrodes 24. For example, processing system 32 may be configured to detect cardiac electrical activity associated with a dominant rotor or divergent activation pattern in the anatomical feature being mapped. Dominant rotors and/or divergent activation patterns may have a role in the initiation and maintenance of atrial fibrillation, and ablation of the rotor path, rotor core, and/or divergent foci may be effective in terminating the atrial fibrillation. Processing system 32 processes the sensed cardiac electrical activity to generate a display of relevant characteristics, such as an isochronal map, activation time map, action potential duration (APD) map, a vector field map, a contour map, a reliability map, an electrogram, a cardiac action potential and the like. The relevant characteristics may assist a user to identify a site suitable for ablation therapy.

Ablation probe 16 includes flexible catheter body 34 that carries one or more ablation electrodes 36. The one or more ablation electrodes 36 are electrically connected to radio frequency (RF) generator 37 that is configured to deliver ablation energy to the one or more ablation electrodes 36. Ablation probe 16 may be movable with respect to the anatomical feature to be treated, as well as structure 20. Ablation probe 16 may be positionable between or adjacent to electrodes 24 of structure 20 as the one or more ablation electrodes 36 are positioned with respect to the tissue to be treated.

Processing system 32 may output data to a suitable device, for example display device 40, which may display relevant information for a user. In some examples, device 40 is a CRT, LED, or other type of display, or a printer. Device 40 presents the relevant characteristics in a format useful to the user. In addition, processing system 32 may generate position-identifying output for display on device 40 that aids the user in guiding ablation electrode(s) 36 into contact with tissue at the site identified for ablation.

Figure 2:
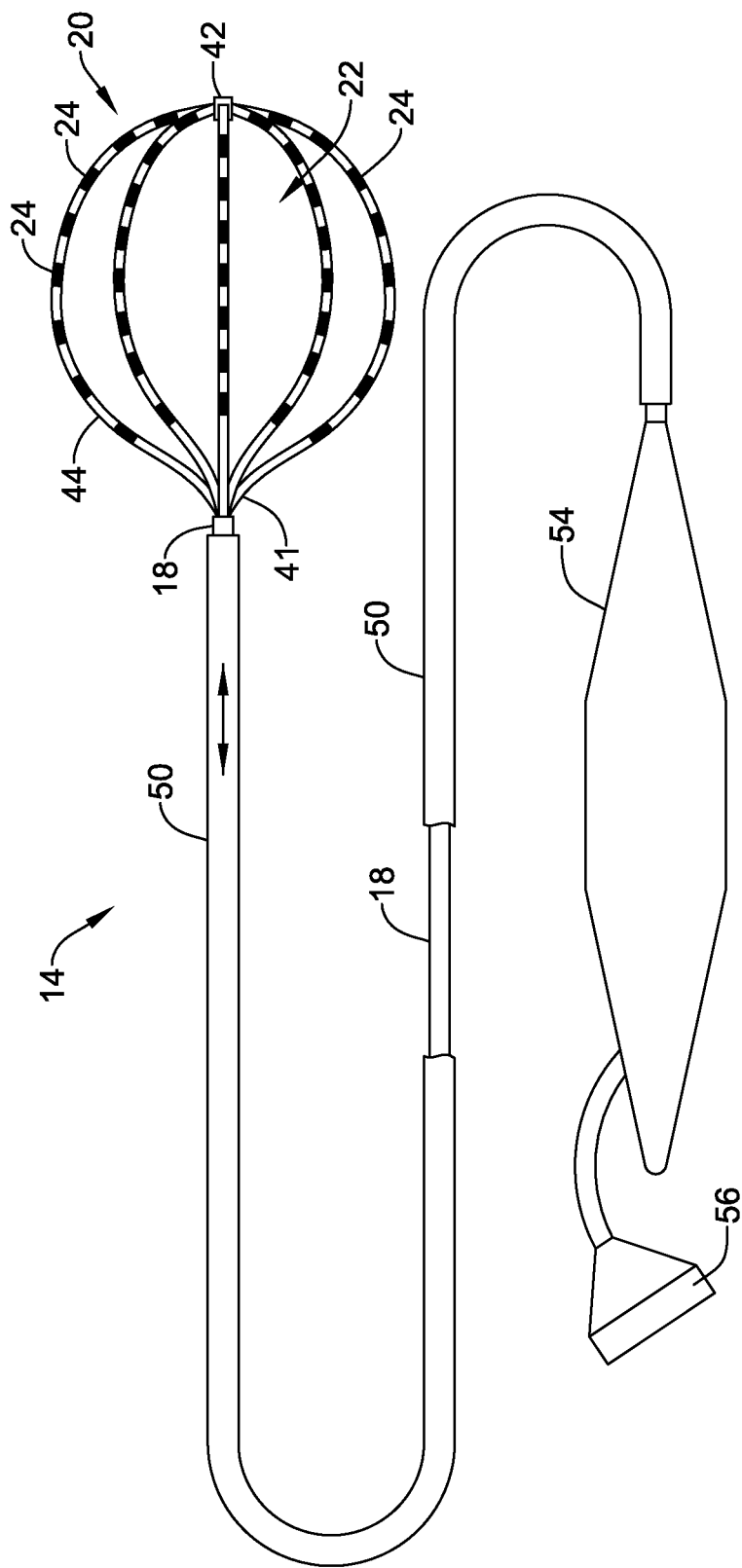
FIG. 2 is a schematic view of an example mapping catheter having a basket functional element carrying structure for use in association with the system of FIG. 1, in accordance with aspects of this disclosure.

FIG. 2 illustrates mapping catheter 14 and shows electrodes 24 at the distal end suitable for use in system 10 shown in FIG. 1. Mapping catheter 14 may include flexible catheter body 18, the distal end of which may carry three-dimensional multiple electrode structure 20 with mapping electrodes or sensors 24. Mapping electrodes 24 may sense cardiac electrical activity, including activation signals, in the myocardial tissue. The sensed cardiac electrical activity may be processed by the processing system 32 to assist a user in identifying the site or sites having a heart rhythm disorder or other myocardial pathology via generated and displayed relevant characteristics. This information can then be used to determine an appropriate location for applying appropriate therapy, such as ablation, to the identified sites, and to navigate the one or more ablation electrodes 36 to the identified sites.

The illustrated three-dimensional multiple electrode structure 20 comprises base member 41 and end cap 42 between which flexible splines 44 generally extend in a circumferentially spaced relationship. As discussed herein, structure 20 may take the form of a basket defining an open interior space 22. In some examples, the splines 44 are made of a resilient inert material, such as Nitinol, other metals, silicone rubber, suitable polymers, or the like and are connected between base member 41 and end cap 42 in a resilient, pretensioned condition, to bend and conform to the tissue surface they contact. In the example illustrated in FIG. 2, eight splines 44 form three dimensional multiple electrode structure 20. Additional or fewer splines 44 could be used in other examples. As illustrated, each spline 44 carries eight mapping electrodes 24. Additional or fewer mapping electrodes 24 could be disposed on each spline 44 in other examples of three dimensional multiple electrode structure 20. In the example illustrated in FIG. 2, structure 20 is relatively small (e.g., 40 mm or less in diameter). In alternative examples, structure 20 is even smaller or larger (e.g., less than or greater than 40 mm in diameter).

Slidable sheath 50 may be movable along the major axis of catheter body 18. Moving sheath 50 distally relative to catheter body 18 may cause sheath 50 to move over structure 20, thereby collapsing structure 20 into a compact, low profile condition suitable for introduction into and/or removal from an interior space of an anatomical structure, such as, for example, the heart. In contrast, moving sheath 50 proximally relative to the catheter body may expose structure 20, allowing structure 20 to elastically expand and assume the pretensed position illustrated in FIG. 2.

A signal wire (not shown) may be electrically coupled to each mapping electrode 24. The signal wires may extend through body 18 of mapping catheter 20 (or otherwise through and/or along body 18) into handle 54, in which they are coupled to external connector 56, which may be a multiple pin connector. Connector 56 electrically couples mapping electrodes 24 to processing system 32. It should be understood that these descriptions are just examples. Some addition details regarding these and other example mapping systems and methods for processing signals generated by a mapping catheter can be found in U.S. Pat. Nos. 6,070,094, 6,233,491, and 6,735,465, the disclosures of which are hereby expressly incorporated herein by reference.

Figure 3:
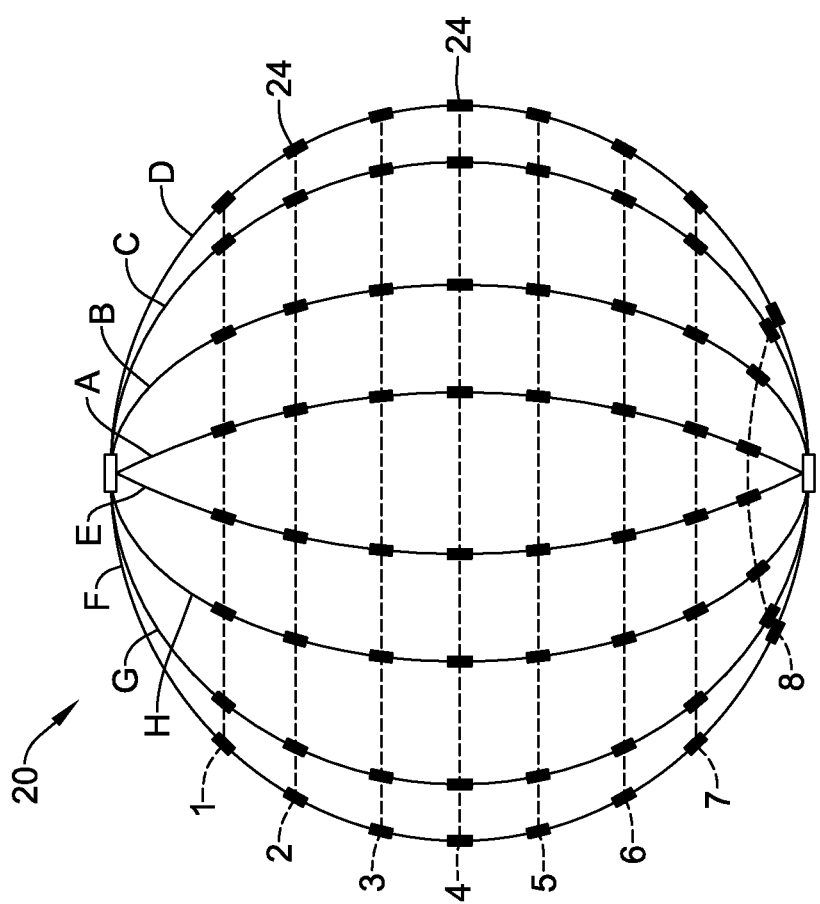
FIG. 3 is a schematic view of an example functional element including a plurality of mapping electrodes, in accordance with aspects of this disclosure.

To illustrate the operation of system 10, FIG. 3 is a schematic side view of an example of basket structure 20 including a plurality of mapping electrodes 24. In the illustrated example, the basket structure includes 64 mapping electrodes 24. Mapping electrodes 24 are disposed in groups of eight electrodes (labeled 1, 2, 3, 4, 5, 6, 7, and 8) on each of eight splines (labeled A, B, C, D, E, F, G, and H). While an arrangement of sixty-four mapping electrodes 24 is shown disposed on basket structure 20, mapping electrodes 24 may alternatively be arranged in different numbers (more or fewer splines and/or electrodes), on different structures, and/or in different positions. In addition, multiple basket structures can be deployed in the same or different anatomical structures to simultaneously obtain signals from different anatomical structures.

After basket structure 20 is positioned adjacent to the anatomical structure to be treated (e.g. left atrium, left ventricle, right atrium, or right ventricle of the heart), processing system 32 is configured to record the cardiac electrical activity from each electrode 24 channel, and the cardiac electrical activity is related to physiological activity of the adjacent anatomical structure. For instance, cardiac electrical activity may include activation signals which may indicate an onset of physiological activity, such as a contraction of the heart. Electrodes 24 sense such cardiac electrical activity which includes activation signals. The cardiac electrical activity of physiological activity may be sensed in response to intrinsic physiological activity (e.g. intrinsically generated electrical signals) or based on a predetermined pacing protocol instituted by at least one of the plurality of electrodes 24 (e.g. delivered electrical signals delivered by a pacing device).

The arrangement, size, spacing and location of electrodes along a constellation catheter or other mapping/sensing device, in combination with the specific geometry of the targeted anatomical structure, may contribute to the ability (or inability) of electrodes 24 to sense, measure, collect and transmit electrical activity of cellular tissue. As stated, because splines 44 of a mapping catheter, constellation catheter or other similar sensing device are bendable, they may conform to a specific anatomical region in a variety of shapes and/or configurations. Further, at any given position in the anatomical region, structure 20 may be manipulated such that one or more splines 44 may not contact adjacent cellular tissue. For example, splines 44 may twist, bend, or lie atop one another, thereby separating splines 44 from nearby cellular tissue. Additionally, because electrodes 24 are disposed on one or more of splines 44, they also may not maintain contact with adjacent cellular tissue. Electrodes 24 that do not maintain contact with cellular tissue may be incapable of sensing, detecting, measuring, collecting and/or transmitting electrical activity information. Further, because electrodes 24 may be incapable of sensing, detecting, measuring, collecting and/or transmitting electrical activity information, processing system 32 may be incapable of accurately displaying diagnostic information. For example, some necessary information may be missing and/or displayed inaccurately.

In addition to that stated above, electrodes 24 may not be in contact with adjacent cellular tissue for other reasons. For example, manipulation of mapping catheter 14 may result in movement of electrodes 24, thereby creating poor electrode-to-tissue contact. Further, electrodes 24 may be positioned adjacent fibrous, dead or functionally refractory tissue. Electrodes 24 positioned adjacent fibrous, dead or functionally refractory tissue may not be able to sense changes in electrical potential because fibrous, dead or functionally refractory tissue may be incapable of depolarizing and/or responding to changes in electrical potential. Finally, far-field ventricular events and electrical line noise may distort measurement of tissue activity.

However, electrodes 24 that contact healthy, responsive cellular tissue may sense cardiac electrical activity such as a change in the voltage potential of a propagating cellular activation wavefront. Further, in a normal functioning heart, electrical discharge of the myocardial cells may occur in a systematic, linear fashion. Therefore, detection of non-linear propagation of the cellular excitation wavefront may be indicative of cellular firing in an abnormal fashion. For example, cellular firing in a rotating pattern may indicate the presence of dominant rotors and/or divergent activation patterns. Further, because the presence of the abnormal cellular firing may occur over localized target tissue regions, it is possible that electrical activity may change form, strength or direction when propagating around, within, among or adjacent to diseased or abnormal cellular tissue. Identification of these localized areas of diseased or abnormal tissue may provide a user with a location for which to perform a therapeutic and/or diagnostic procedure. For example, identification of an area including reentrant or rotor currents may be indicative of an area of diseased or abnormal cellular tissue. The diseased or abnormal cellular tissue may be targeted for an ablative procedure. An activation time map may be used to identify areas of circular, adherent, rotor or other abnormal cellular excitation wavefront propagation.

As discussed above, in some instances, it may be desirable to filter the sensed cardiac electrical activity, such as by removing far-field signals from the signals sensed by electrodes 24. Generally, system 10 may be configured to gather a source signal and a reference signal. The source signal, sensed for instance by electrodes 24, comprises both a near-field signal component and a far-field signal component. The far-field signal component may be a far-field signal artifact. For instance, the far-field signal may become distorted as the far-field signal propagates from its source to electrodes 24. This distorted far-field signal sensed by electrodes 24 is the far-field signal artifact present in the source signal. System 10 may additionally sense a reference signal, which may be a representation of the far-field signal component. System 10 may further process the reference signal to determine an estimation of the far-field signal artifact and subtract the estimated far-field signal artifact from the source signal, thereby leaving only the near-field signal component of the source signal.

In some examples, the near-field signal component referenced herein may be an atrial signal sensed by electrodes 24 disposed in an atrium of a heart. In such examples, the far-field artifacts may be ventricular signals conducted through the tissue of the patient and received by electrodes 24, along with the near-field signal component. In such cases, it may be desirable to remove the sensed ventricular signals from the signals sensed by electrodes 24 to get a clearer picture of the atrial signals. However, the techniques described herein are more broadly applicable than with respect to atrial signals and ventricular signals. Accordingly, this disclosure may use the term near-field signal component to describe a signal sensed by an electrode which is generated adjacent to the electrode and far-field signal artifact to describe a signal that is generated remote from the electrode that is still sensed by the electrode.

In order to gather a reference signal, processing system 32 may further include external electrodes 15, as shown in FIG. 1. External electrodes 15 may be electrodes external to mapping probe 14. In some examples, external electrodes 15 may be configured in a standard 12-lead surface EKG configuration. During times of atrial flutter or atrial fibrillation, the atrial signals generated by the atria may be erratic and unsynchronized. Accordingly, atrial signals reaching external electrodes 15 on the surface of the patient may tend to become minimized relative to ventricular signals because the erratic and unsynchronized atrial signals may cancel each other, at least to some extent. In some examples, external electrodes 15 may be configured in other configurations, such as in the Frank configuration, with three electrodes configured in completely orthogonal directions.

In other examples, external electrodes 15 may be electrodes which are internal to the patient's body. For instance, external electrodes 15 may be electrodes disposed within a ventricle or other chamber of the heart. In still other examples, system 10 may not include external electrodes 15. In such examples, electrodes 24 may sense the reference signal. Processing system 32 may additionally processes the reference signals sensed by electrodes 24, or external electrodes 15 disposed within other chambers of the heart, by averaging multiple sensed signals in order to minimize the near-field atrial signals.

The above techniques for gathering a reference signal are only some possible examples. Generally, the techniques disclosed herein may be performed using any signal as a reference signal. However, using a reference signal with a few particular qualities may help to increase the accuracy of the described techniques. First, the reference signal may comprise at least some data from three dimensions. Further, the more complete the data from each dimension, generally the higher the accuracy of the described techniques may tend to be. For example, such three dimensional data may be obtained by using a standard 12-lead configuration or the Frank lead configuration, as described previously. Additionally, the reference signal should be uncorrelated with respect to intrinsic atrial electrical activity. That is not to say that the reference signal needs to be completely uncorrelated with respect to intrinsic atrial electrical activity. Rather, the lower the correlation between the reference signal and the intrinsic atrial electrical activity, generally the higher the accuracy of the described techniques. For example, as described above, signals sensed by surface electrodes during atrial flutter or fibrillation may be sufficient sources of low-correlation signals. However, in other examples, processing system 32 may process other sensed signals to reduce atrial electrical activity in order to generate a reference signal.

Figure 4:
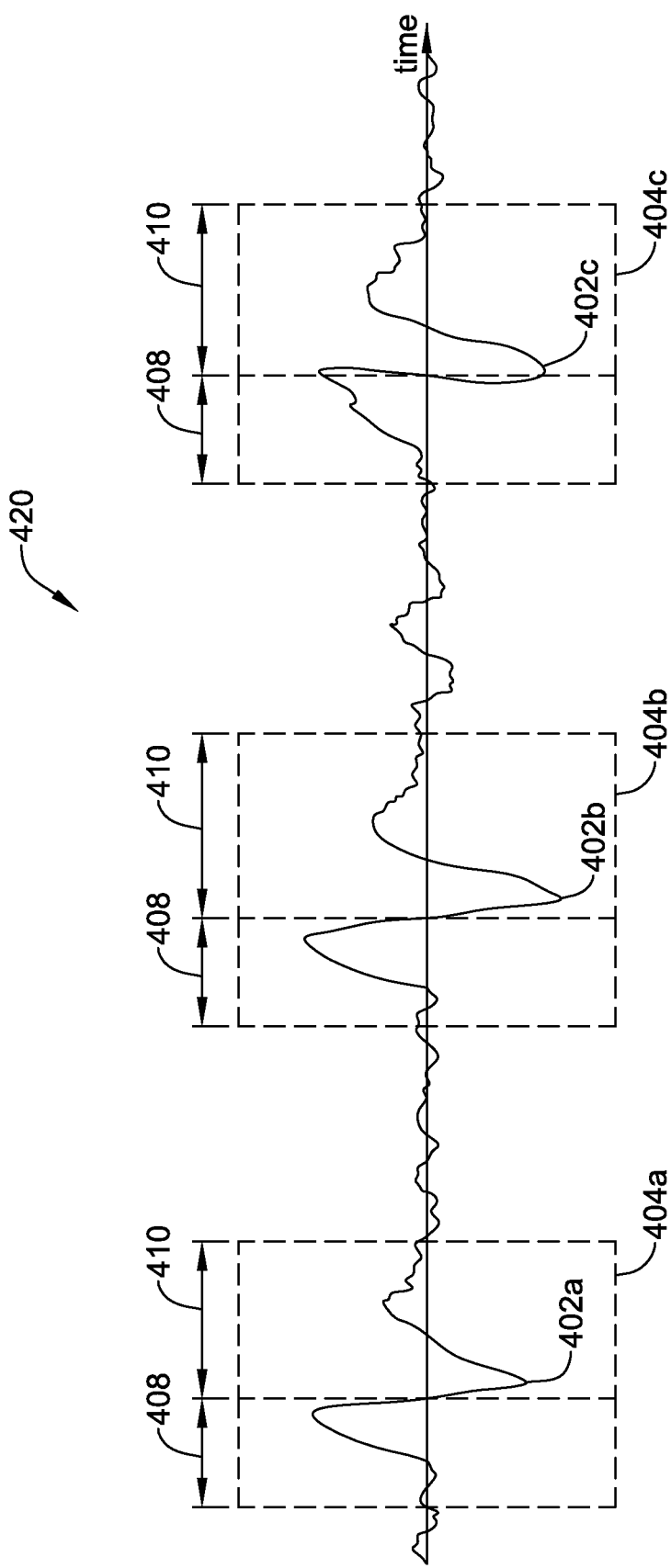
FIG. 4 is an illustration of sensed cardiac electrical signals, in accordance with aspects of this disclosure.

After gathering a reference signal, either by sensing a signal with appropriate characteristics, or by processing a signal to generate a signal with appropriate characteristics, system 10 may then generate one or more windows around detected beats, as shown in FIG. 4. For example, system 10 may use a peak detector and/or a QRS detector to determine R-waves and/or QRS complexes, for example QRS complexes 402a, 402b, and 402c, present in reference signal 420. System 10 may then generate a beat window surrounding each detected R-wave and/or QRS complex. The beat window may extend a length 408 from a reference point to a point prior to the reference point. The beat window may additionally extend a length 410 from a reference point to a point subsequent to the reference point. In some examples, the reference point may be a peak of the R-wave. In other examples, the reference point may be a point of maximum negative slope of the QRS complex. In other examples, the reference point may be any other identifiable point within or near a detected R-wave and/or QRS complex.

In some examples, the beat windows may have predetermined dimensions. For example length 408 may be one-hundred milliseconds, and length 410 may be three-hundred milliseconds. However, in other examples, length 408 may be fifty, two-hundred, or three-hundred milliseconds, or any other suitable length of time. Similarly, in other examples, length 410 may be fifty, one-hundred, or two-hundred milliseconds, or any other suitable length of time. In some examples, lengths 408 and 410 may be defined by a user, thereby allowing the beat window size to be adjustable. For instance, a user may enter input into display 40 specifying values for length 408 and length 410.

Figure 5:
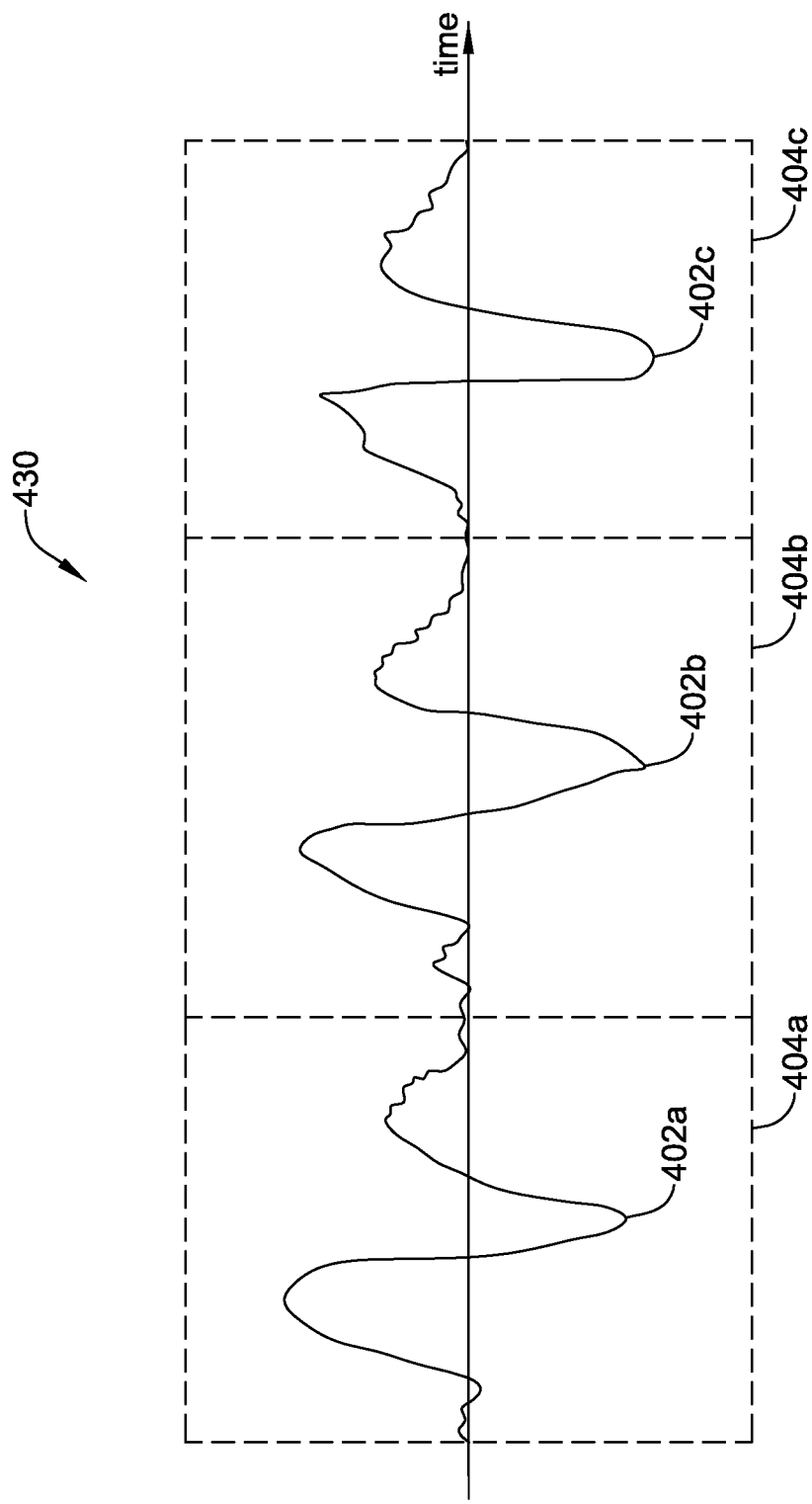
FIG. 5 is an illustration of modified sensed cardiac electrical signals, in accordance with aspects of this disclosure.

After generating beat windows around the identified R-waves and/or QRS complexes, system 10 may concatenate the beat windows, as shown in FIG. 5. For example, system 10 may eliminate any data which does not fall within a beat window, thereby creating a new signal comprised of only signal data which fell within a beat window. The new signal may be termed the concatenated reference signal and is represented by concatenated reference signal 430 in FIG. 5.

System 10 may additionally gather one or more source signals. For instance, system 10 may sense a signal with each of electrodes 24. Each of these sensed signals may be a source signal. In some examples, system 10 may gather the one or more source signals sensed by electrodes 24 at the same time as gathering the reference signal. Accordingly, the data represented by the one or more source signals and the reference signal may represent information about the same cardiac cycle or cycles. After determining one or more beat windows in the reference signal, system 10 may determine beat windows in each of the one or more source signals at time ranges corresponding to those time ranges of the beat windows formed in the reference signal. As with the reference signal, system 10 may concatenate the determined beat windows in each of the one or more source signals, thus forming one or more concatenated source signals. This ensures that the data in the one or more source signals is time-aligned with the data in the reference signal.

System 10 may proceed to perform one or more processing techniques on the concatenated reference signal. For instance, system 10 may employ one of a number of linear or non-linear dimensionality reduction techniques on the concatenated reference signal. One linear dimensionality reduction technique that system 10 may employ is principal component analysis (PCA). However, in other examples, system 10 may employ other known linear or non-linear dimensionality reduction techniques to reduce the dimensionality of the concatenated reference signal.

As described previously, the reference signal may be a representation of the far-field signal component of the source signal. The morphology of the reference signal may become distorted as it propagates from the tissue generating the reference signal through the body before being sensed by electrodes 24 as a far-field artifact. Accordingly, the far-field signal artifact present in the source signal may be morphologically different than the sensed reference signal. For example, the body tissue may be modeled as an R-C network through which the heart signal propagates before being sensed by electrodes 24. It is the propagation through such an R-C network that imparts time and/or spatial dispersion on the reference signal as it propagates throughout the body tissue. Accordingly, system 10 may apply an inverse system in order to compensate for such morphological differences between the sensed reference signal and the far-field signal artifact present in the source signal to generate an estimate of the far-field signal artifact present in the source signal based on the sensed reference signal. System 10 may then subtract out the estimated far-field signal artifact from the source signal.

Figure 6A:
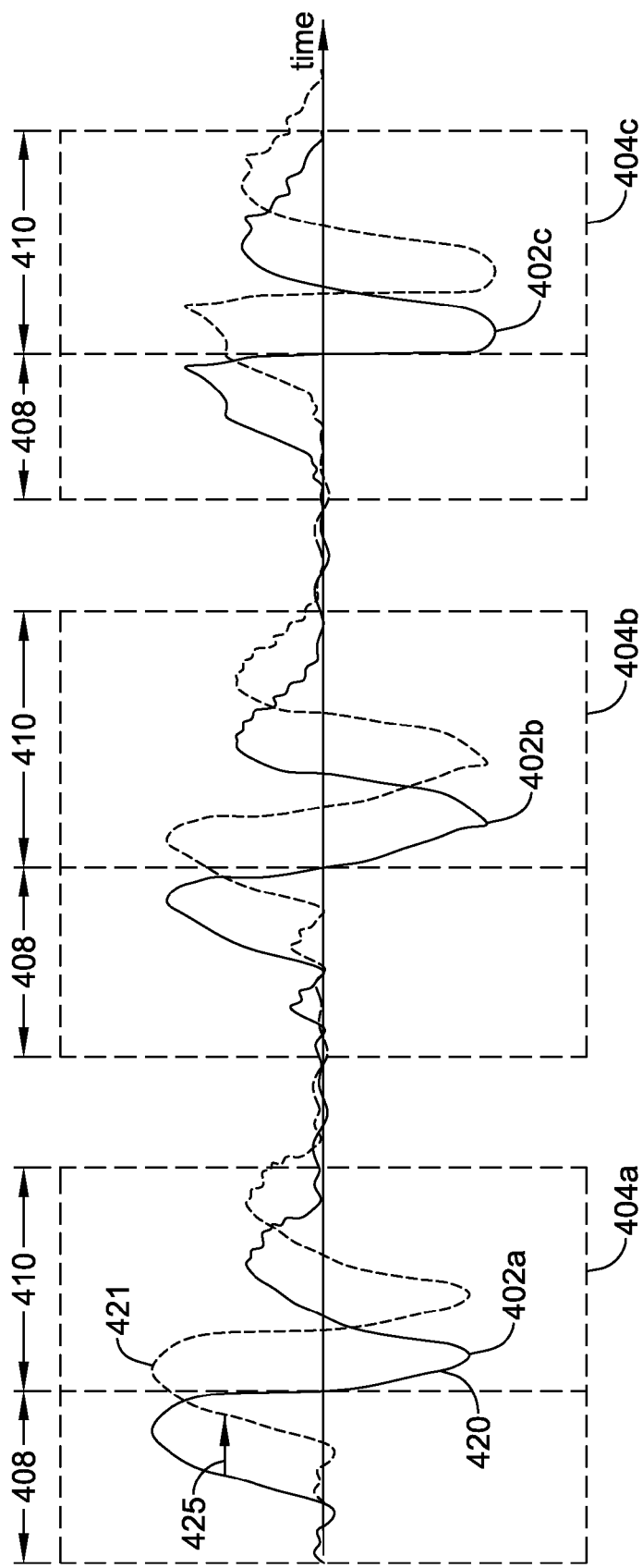
FIG. 6A is another illustration of multiple cardiac electrical signals, in accordance with aspects of this disclosure.
Figure 6B:
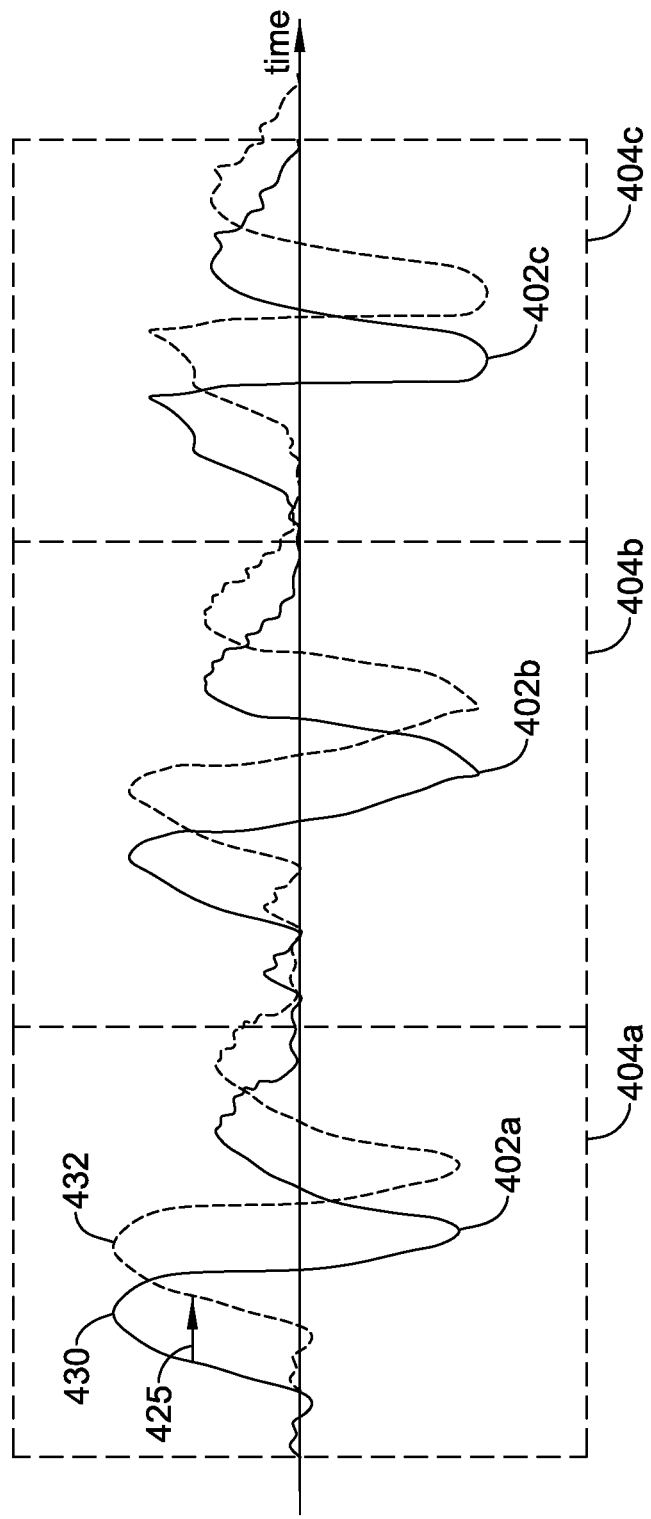
FIG. 6B is another illustration of multiple cardiac electrical signals, in accordance with aspects of this disclosure

In some examples, system 10 may compensate for any dispersion of the reference signal by generating one or more shifted copies of the reference signal. For example, as depicted in FIG. 6A, system 10 may generate a copy of reference signal 420 that is shifted in time to the right, as evidenced by arrow 425, which may be termed shifted reference signal 421. System 10 may further form beat windows in reference signal 421 at the same (un-shifted) time ranges as in reference signal 420. FIG. 6A illustrates this concept as beat windows 404a-c are the same beat windows as depicted in FIGS. 4 and 5, which were formed around QRS waves 402a-c, as opposed to being formed based on features of shifted reference signal 421. System 10 may further concatenate the beat windows formed for shifted reference signal 421. This may result inshifted concatenated reference signal 432, as displayed in FIG. 6B. In other examples, system 10 may generate a copy of concatenated reference signal 430 and then shift concatenated reference signal 430 in time to the right to generate a shifted concatenated reference signal instead of generating a shifted copy of reference signal 420 and then concatenating the shifted reference signal.

System 10 may shift reference signal 420 or concatenated reference signal 430 by simply shifting the individual samples of the corresponding signal by some amount of samples, which may be termed a shift value. Some example shift values include five, eight, ten, eleven, fifteen, and twenty samples; however any number of samples may be used in other examples. In some examples, the shift value may be predetermined. In other examples, the shift value may be a user defined value. For instance, a user may enter a shift value into display 40. Processing system 32 may receive such a shift value and use the input shift value for generating shifted copies of concatenated reference signal 430.

In some examples, system 10 may generate a plurality of shifted concatenated reference signals 432, either by shifting reference signal 420 and then concatenating the shifted signals or by shifting concatenated reference signal 430, as described above. To generate the plurality of shifted concatenated reference signals, system 10 may shift the reference signal 420 by a number of samples that are multiples of the first shift value. For example, if system 10 generates three shifted copies of concatenated reference signal 430, the first copy may be shifted by a shift value of eleven samples. The second copy may shifted by twice the shift value, which is twenty-two samples. The third copy may be shifted by three-times the shift value, which is thirty-three samples. In some examples, system 10 may generate copies that are shifted in the opposite direction of shifted concatenated reference signal 432. For example, system 10 may use negative multiples of the shift value for generating such copies that are shifted earlier in time.

In some examples, system 10 may generate a predetermined number of shifted concatenated reference signals 432. For instance, system 10 may generate five, ten, fifteen, or twenty shifted copies of concatenated reference signal 430, with any number of the shifted copies being shifted earlier or later than the concatenated reference signal. In other examples, a user may specify how many shifted concatenated reference signals 432 system 10 generates. For example, a user may enter into display 40 a number of shifted copies for system 10 to generate. Additionally, a user may enter a number of shifted copies that are shifted earlier with respect to concatenated reference signal 430 (to the left of concatenated reference signal 430 as depicted in FIG. 6) and later with respect to concatenated reference signal 430. In such examples, system 10 may generate sequential shifted concatenated reference signals 430 by incrementing the multiple of the shift value. For instance, if a user entered five shifted copies with two copies shifted earlier and three copies shifted later than concatenated reference signal 430, system 10 may generate a first shifted concatenated reference signal 432 using a multiple of the shift value of negative two. System 10 may then increment the multiple of the shift value by one and generate another shifted concatenated reference signal 432 using a multiple of the shift value of negative one. System 10 may continue this process until system 10 has generated an amount of shifted concatenated reference signal 432 equal to the number input by the user. When generating such shifted copies, system 10 may skip generating a shifted concatenated reference signal 432 if the multiple of the shift value is zero.

Once system 10 has generated one or more shifted concatenated reference signals 432, system 10 may then project back the concatenated reference signal and, in some examples, each of the shifted copies of the concatenated reference signal onto each of the one or more source signals using an error minimization technique. This may result in determining a signal which results in a minimization of the reference signal artifact in the source signal. One technique system 10 may employ for this process is to form a projection matrix comprising the concatenated reference signal and the one or more shifted copies of the concatenated reference signal.

Figure 7:
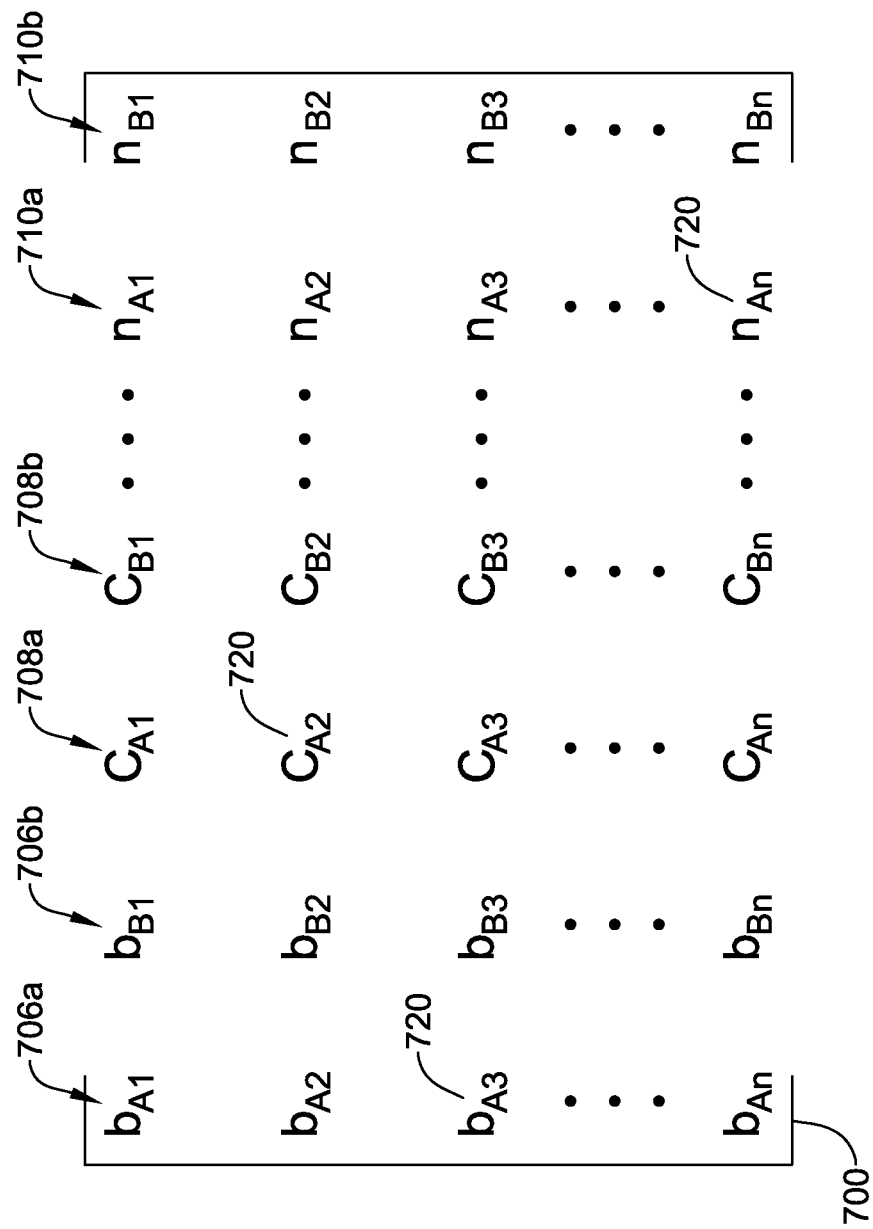
FIG. 7 is an illustration of a convolution matrix, in accordance with aspects of this disclosure.

In at least some examples, the projection matrix may take the form of a convolution matrix. FIG. 7 depicts example convolution matrix 700. Convolution matrix 700 may include a number of columns, with each column representing a signal or signal component. For example, column 706a may represent a first component of the concatenated reference signal. Each symbol 720 of each column may represent an individual sample of the signal or signal component. Accordingly, the "$b_{A1}$" symbol of column 706a may represent the first sample of the concatenated reference signal, the "$b_{A2}$" symbol of column 706a may represent the second sample of the concatenated reference signal, and so on. Column 706b may represent a second component of the concatenated reference signal. Accordingly, in the example of FIG. 7, the concatenated reference signal comprises two components. However, in other examples, the concatenated reference signal may comprise more or fewer components.

Columns 708a, 708b through 710a, 710b may all represent components of shifted copies of the concatenated reference signal. For example, column 708a may represent a first component of a first shifted copy of the concatenated reference signal. Column 708b may represent a second component of the first shifted copy of the concatenated reference signal. Columns 710a and 710b may represent first and second components of a second shifted copy of the concatenated reference signal. Although only explicitly depicted in FIG. 7 as including two shifted copies of the concatenated reference signal, it should be understood that convolution matrix 700 may include an arbitrary amount of shifted copies of the concatenated reference signal.

Figure 8:
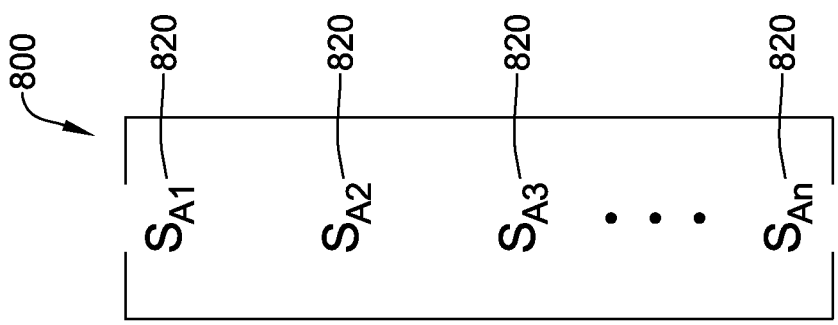
FIG. 8 is an illustration of an example column vector, in accordance with aspects of this disclosure.

The concatenated source signal may also be formed into a matrix. For example, the concatenated source signal may be sampled and arranged into a matrix such as matrix 800 as shown in FIG. 8. Each element 820 of matrix 800 is an individual sample of the concatenated source signal and the samples may be aligned with elements 720 of matrix 700, for instance with the first sample positioned at the top of matrix 800 and the last sample placed at the bottom of matrix 800. In examples where the concatenated source signal includes only a single component, matrix 800 may be a single column matrix, termed a column vector (as in FIG. 8).

Figure 9:
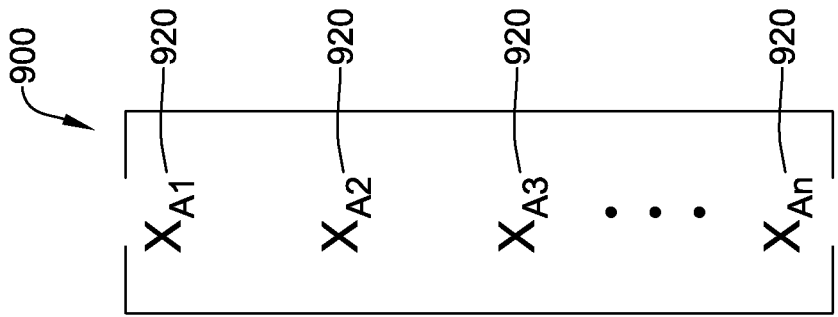
FIG. 9 is another illustration of an example column vector, in accordance with aspects of this disclosure.

System 10 may additionally generate a column vector, such as column vector 900 of FIG. 9, which includes linear combination coefficients, represented by elements 920, as will be described below. Vector 900 may be arranged to have the same number of elements as convolution matrix 700 has components (columns). For ease of reference below, matrix 700 may be referred to as matrix $H_b$, matrix 800 may be referred to as vector b, and vector 900 may be referred to as vector x. When matrix $H_b$ and vector x are multiplied together, they may produce a vector-matrix product called vector b', as in equation (1) below.

$$H_b x = b' \quad (1).$$

Vector b' may be of same the dimension as vector b, i.e. matrix 800. Generally speaking, vector b' may be an estimate or projection of vector b, and may sometimes be referenced as the estimate of the far-field signal artifacts of the concatenated source signal.

System 10 may be configured to determine a set of linear combination coefficients for vector x (e.g. the elements of vectors x) that result in an optimal vector b'. The process system 10 may use to find such linear combination coefficients may commonly be called "projection." Some well-known techniques in the art used in such a process include methods of least-squares regression, constrained least-squares, maximum-likelihood estimation, and linear programming. Depending on the specific technique used, the "optimal" vector b' may be different—e.g. considered optimal for different purposes or reasons. In at least the case of least squares projection, the solution for x that results in an optimal vector b' results in a vector b' that most closely correlates to vector b.

Relating the above discussed matrices and vectors back to the source and reference signals, vector b, as described above, is a representation of the concatenated source signal. The concatenated source signal, as mentioned previously, is comprised of a mixture of near field signal components and far-field signal artifacts. Matrix $H_b$ includes one or more concatenated reference signals and shifted concatenated reference signals, which may include components that are representative of the far-field signal artifacts present in the concatenated source signal. Determining vector b' from matrix $H_b$, then, results in a signal (vector b') which has components that are closely correlated with the far-field artifacts of the concatenated source signal.

Once system 10 has found the set of linear combination coefficients (e.g. the components of vector x) that produce an optimal vector b', system 10 may then determine a contiguously sampled signal that is an estimate of the far-field signal artifacts of the contiguously sampled source signal. For instance, system 10 perform the above described projection with beat windowed signals—matrix $H_b$ and vector b' both contain representations of concatenated beat-windowed signals. After determining the linear combination coefficients for vector x, system 10 may generate additional matrix $H_c$, where the columns of matrix $H_c$ represent the contiguously sampled (e.g. non-concatenated) reference signal (or signal components) and the contiguously sampled shifted reference signals (or signal components). In other words, matrix $H_b$ and matrix $H_c$ may be similar except that matrix $H_b$ contains representations of the concatenated beat-windowed reference and shifted reference signals and matrix $H_c$ contains representations of the contiguously sampled reference and shifted reference signals. System 10 may then multiply vector x, containing the determined linear combination coefficients, with matrix $H_c$, producing a contiguously sampled signal (vector c') as shown in equation (2).

$$H_c x = c' \tag{2}$$

Vector c' may be similar to vector b', except that vector c' represents a contiguously sampled signal. In equation (2), system 10 used the vector x previously found to optimize the correlation between vector b' and the biological source signal. Accordingly, vector c' represents the components of matrix $H_c$ that most closely correlate with the biological source signal. As with matrix $H_b$, matrix $H_c$ may include components that are representative of the far-field signal artifacts present in the original source signal (e.g. the contiguously sampled source signal). Accordingly, vector c' is comprised of components that are closely correlated with the far-field signal artifacts of the original source signal. Vector c' may also be termed the estimate of the far-field signal artifacts in the source signal.

System 10 may finally subtract vector c' from the original source signal to obtain a signal that is representative of the near-field signal components of the original source signal. That is, as vector c' is an estimate of the far-field signal artifacts in the original source signal, subtracting vector c' from the original source signal may leave only the near-field signal components of the original source signal. This difference between vector c' and the original source signal may be termed the residual signal.

Having produced a residual signal for a single source signal, system 10 may perform a similar process for each of the source signals. For instance, as described above, system 10 may include sixty-four electrodes which gather sixty-four source signals. Additionally as described above, system 10 may further employ these signals in other applications such as for determining areas of a heart to ablate.

As described previously, in some procedures, this near-field signal component is the signal of interest in determining areas of the heart to ablate. For example, system 10 may additionally determine one or more activation times for each signal sensed by electrodes 24 in order to generate one or more visual maps depicting information about the heart. For example, system 10 may operate according to the techniques described in "MEDICAL DEVICES FOR MAPPING CARDIAC TISSUE", filed Mar. 11, 2014, with a provisional application No. 61/951,266, and is commonly owned. Removing the far-field signal components of the sensed source signals may allow systems to more accurately determine activation timings and/or generate the one or more maps.

In some situations, however, the reference signal may also include components that are representative of the near field signal components of the source signal. In such situations, matrices $H_b$ and $H_c$ will therefore also contain components which are representative of the near-field signal components of the source signal. Any resulting vectors c' and residual signals, then, may not be so cleanly split between the far-field signal artifacts and near-field signal components of the source signal. The earlier discussed processing techniques described some methods of de-emphasizing the near-field signal components and/or emphasizing the representations of the far-field signal artifacts present in the reference signal for generating matrices $H_b$ and $H_c$. For example, performing PCA on the reference signal is one way of emphasizing the representations of the far-field signal artifacts and/or de-emphasizing the near-field signal components (being relative to the source signal), present in the reference signal. Thus, performing PCA may serve to enhance the correlation between the reference signal and the far-field artifacts present in the source signal. System 10 may employ other techniques, however, to serve a similar end—either in addition to or instead of such processing techniques.

Figure 10:
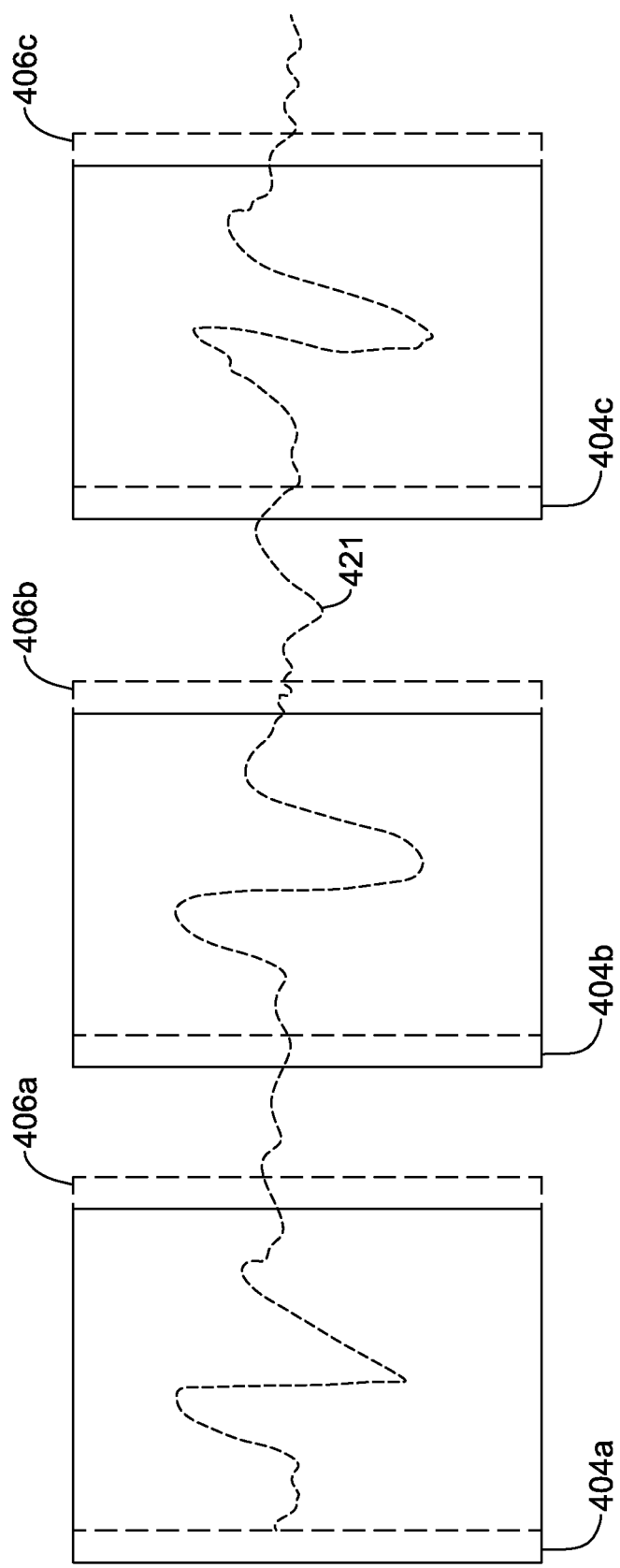
FIG. 10 is an illustration of example beat windows, in accordance with aspects of this disclosure.

For example, system 10, may determine multiple vector b's for a given source signal. As described above, matrix $H_b$ may comprise one or more shifted concatenated reference signals, where each shifted concatenated reference signal has been shifted by a number of samples equal to a multiple of a shift value. In some examples, system 10 may further generate multiple matrices $H_b$ by shifting the generated beat windows. For instance, as described above, when generating shifted reference signals, system 10 kept the beat windows centered around the detected QRS waves or peaks in the original reference signal. To generate additional matrices $H_b$, system 10 may use the generated shifted reference signals, except move the beat windows within the shifted reference signals as shown in FIG. 10. FIG. 10 shows shifted reference signal 421 with beat windows 404a-c. System 10 may shift beat windows 404a-c to the right, resulting in beat windows 406a-c. By shifting the beat windows in this way, system 10 is capturing slightly different portions of the shifted reference signals for use in the additional matrices $H_b$. In generating a first additional matrix $H_b$, system 10 may shift beat windows 404a-c by a single sample. In generating a second additional matrix $H_b$, system 10 may shift beat windows 404a-c by two samples. In some examples, system 10 may generate additional matrices in this manner equal to one less than the shift value.

System 10 may then perform a similar process to that described above for generating an optimal vector b' for each of the generated additional matrices $H_b$, thereby producing a number of vectors b' for each source signal. In such examples, system 10 may further determine corresponding error vectors e, as shown in equation (3).

$$b = b' + e \tag{3}$$

Vector b, as described previously, represents the concatenated source signal, and vector b' represents the output of equation (1). Error vector e, then, may represent the difference between vector b and vector b', and to the extent that vector b' includes components that are closely correlated to the far-field signal artifact present in the concatenated source signal, error vector e may represent the near-field signal component present in the concatenated source signal. Although, as mentioned previously, in some situations, vector b' and vector e may both contain a mixture of near-field signal components and representations of far-field signal components.

After generating a number of vectors b' for each concatenated source signal, system 10 may further create an average beat window for each vector e by averaging the signals in each beat window for a given vector e. For example, as matrix $H_b$ comprises signals made up of concatenated beat windows, the generated vectors b', and thus vectors e, also are comprised of concatenated beat windows. Accordingly, system 10 may then create an average beat window for each of the vectors e. Averaging the beat windows for each vector e may tend to minimize any near-field signal component in vectors e and emphasize any present far-field signal artifacts. System 10 may then perform any of a number of well-known error minimization techniques, such as RMS, mean absolute error, or the like, to determine which of vectors e is the least correlated with its corresponding matrix $H_b$—thereby being the vector e with the least correlation to the far-field artifacts present in the source signal and the vector e with the greatest correlation to the near field signal components of the source signal.

Figure 11:
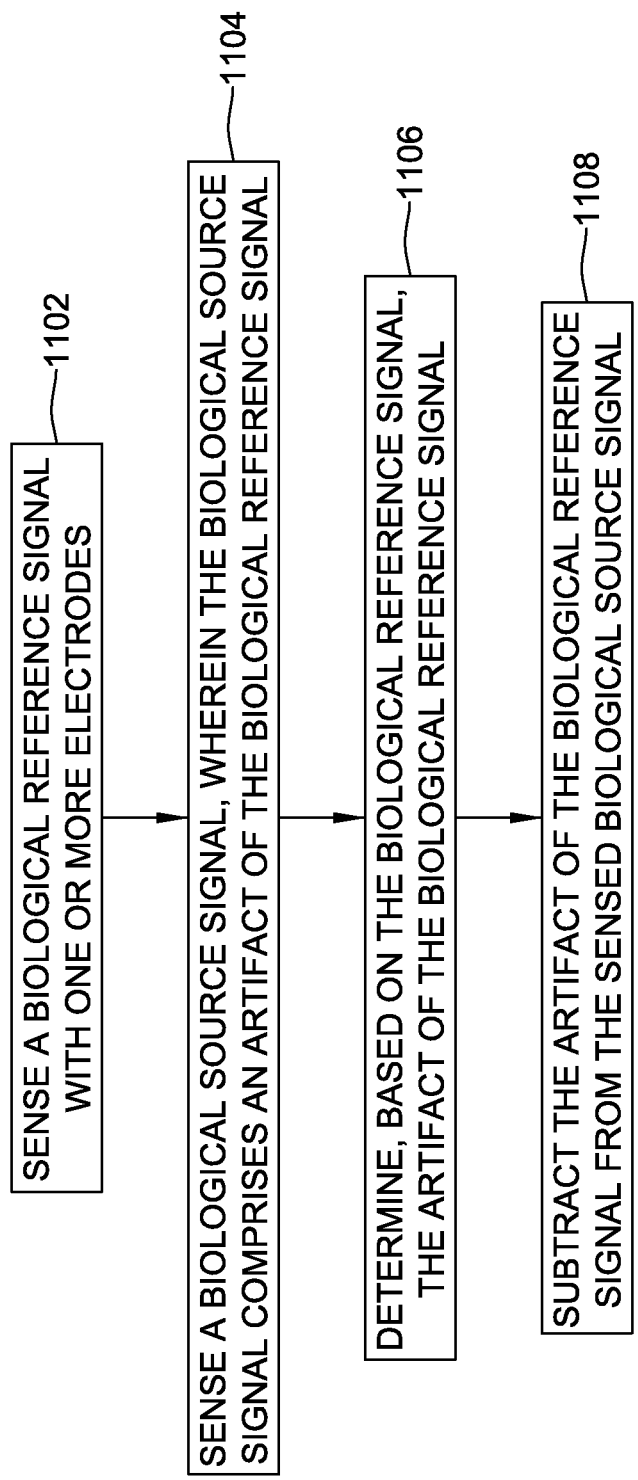
FIG. 11 is an illustrative technique in accordance with this disclosure that may be performed by a catheter system, such as that depicted in FIG. 1.

FIG. 11 is a flow diagram of an illustrative technique that may be implemented by a catheter system such as shown in FIG. 1. Although the method of FIG. 11 will be described with respect to the catheter system of FIG. 1, the illustrative method of FIG. 11 may be performed by any suitable catheter or medical device system.

In some examples, a catheter device, for instance catheter system 10, may include electrodes 24 which are disposed within a heart. System 10 may be configured to sense a biological reference signal with electrodes 24, as shown at 1102. System 10 may additionally be configured to sense a biological source signal, wherein the biological source signal comprises an artifact of the biological reference signal, as shown at 1104. System 10 may further be configured to determine, based on the biological reference signal, the artifact of the biological reference signal, as shown at 1106. For example, system 10 may generate one or more shifted copies of the biological reference signal and back project the biological reference signal and the one or more shifted copies of the biological reference signal onto the biological source signal. In other examples, system 10 may determine the artifact of the biological reference signal in other ways. Finally, system 10 may subtract the artifact of the biological reference signal from the sensed biological source signal, as shown at 1108.

Figure 12:
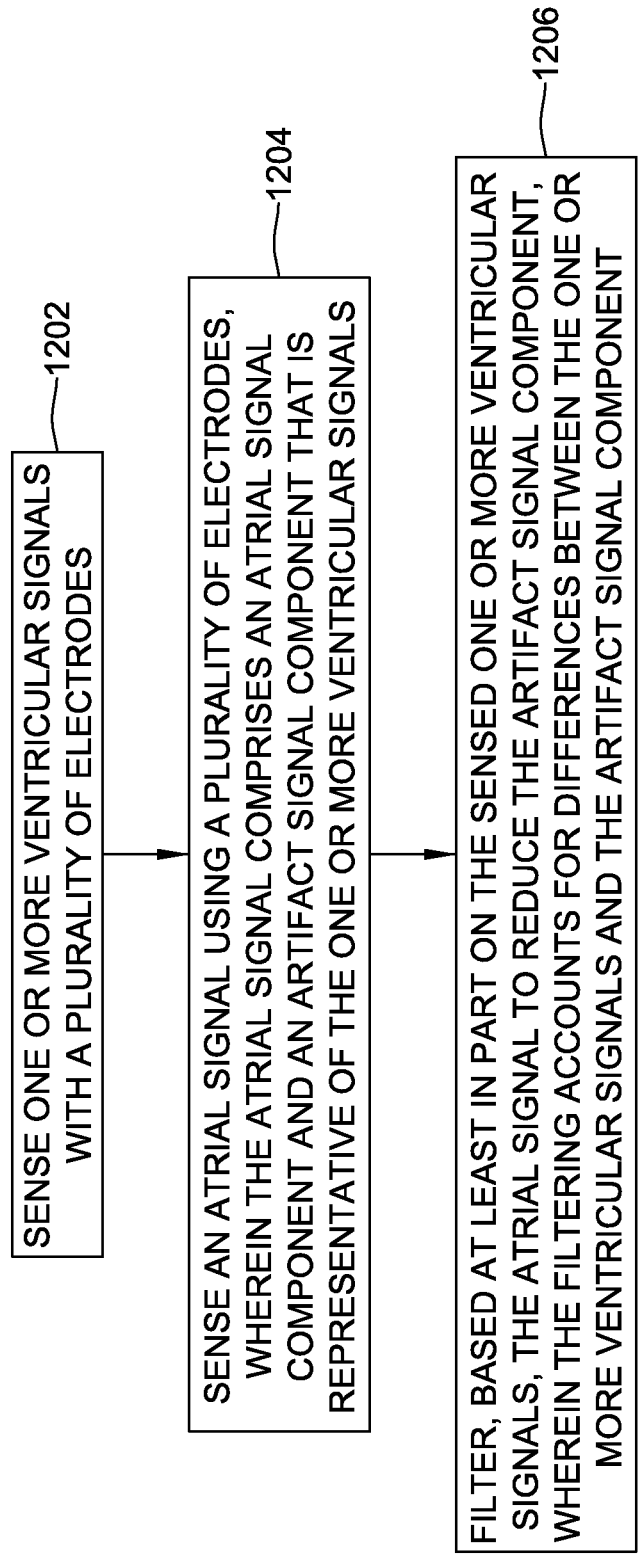
FIG. 12 is another illustrative technique in accordance with this disclosure that may be performed by a catheter system, such as that depicted in FIG. 1.

FIG. 12 is a flow diagram of an illustrative method that may be implemented by a catheter system such as shown in FIG. 1. Although the method of FIG. 12 will be described with respect to the catheter system of FIG. 1, the illustrative method of FIG. 12 may be performed by any suitable catheter system.

In some examples, a catheter device, for instance catheter system 10, may include electrodes 24 which are disposed within a heart. System 10 may be configured to sense one or more ventricular signals with a plurality of electrodes, as shown at 1202. System 10 may further be configured to sense an atrial signal using a plurality of electrodes, wherein the atrial signal comprises an atrial signal component and an artifact signal component that is representative of the one or more ventricular signals, as shown at 1204. Finally, system 10 may be configured to filter, based at least in part on the sensed one or more ventricular signals, the atrial signal to reduce the artifact signal component, wherein the filtering accounts for differences between the one or more ventricular signals and the artifact signal component, as shown at 1206.

The above described techniques represent only a few example techniques contemplated by this disclosure. In other examples, system 10 may process the source and reference signals to a lesser extent. For example, the techniques described herein may used without determining beat windows and producing concatenated signals. Instead, in such examples, system may perform PCA analysis on the unmodified reference signal and perform the back projection with complete source signals and a complete reference. Additionally, in other examples, system 10 may not employ PCA or any other dimensionality reduction technique before back projecting. In some instances, such examples may produce results with sufficient accuracy that such additional steps are not necessary.

However, in other examples, system 10 may perform additional processing of the source and/or reference signals. For example, system 10 may band-pass filter or otherwise perform well-known techniques in the art in order to reduce any noise interference present in the source and/or reference signals.

Additionally, although the above described techniques have been described with respect to cardiac electrical signals, the process is not limited in applicability to only cardiac electrical signals. The techniques described herein may be applicable to removing any far-field signal artifacts that are morphologically different than the far-field signal from a source signal including both a near-field signal component of interest and an undesirable far-field artifact. For example, the techniques described herein may be applicable to sensing electrical signals generated by a brain of a patient and determining which components of a source signal are generated by a localized area of the brain and which components of the source signal are due to far-field signals conducted to the localized area.

What is claimed is:

1. A method for removing a far-field signal component of a cardiac source signal, the method comprising:
   sensing a biological reference signal with one or more electrodes;
   sensing a cardiac source signal, wherein the cardiac source signal includes a near-field component and a far-field component;
   estimating, based on the sensed biological reference signal, the far-field component of the sensed cardiac source signal; and
   subtracting the estimated far-field component of the sensed cardiac source signal from the sensed cardiac source signal.

2. The method of claim 1, wherein estimating, based on the sensed biological reference signal, the far field component comprises compensating for differences between the sensed biological reference signal and the far-field component of the sensed cardiac source signal.

3. The method of claim 2, wherein compensating for differences between the sensed biological reference signal and the far-field component of the sensed cardiac source signal comprises generating one or more shifted copies of the sensed biological reference signal.

4. The method of claim 3, wherein compensating for differences between the sensed biological reference signal and the far-field component of the sensed cardiac source signal comprises: generating, based at least in part on the generated one or more shifted copies of the sensed biological reference signal, an estimated artifact of the sensed biological reference signal.

5. The method of claim 4, wherein subtracting the estimated far-field component of the sensed cardiac source signal from the sensed cardiac source signal comprises subtracting the estimated artifact of the sensed biological reference signal from the sensed cardiac source signal.

6. The method of claim 4, wherein generating, based at least in part on the generated one or more shifted copies of the sensed biological reference signal, an estimated artifact of the sensed biological reference signal comprises:
   forming a projection matrix comprising the sensed biological reference signal and one or more shifted copies of the sensed biological reference signal;
   determining a set of linear combination coefficients using a projection technique; and
   forming the estimated artifact of the sensed biological reference signal from the projection matrix and the set of linear combination coefficients.

7. The method of claim 6, wherein the projection technique comprises one or more of: least-squares regression;

constrained least-squares; maximum likelihood estimation; non-linear programming; and linear programming.

8. The method of claim 4, wherein generating, based at least in part on the generated one or more shifted copies of the sensed biological reference signal, an estimated artifact of the sensed biological reference signal comprises:
generating a convolution matrix H comprising the sensed biological reference signal and one or more shifted copies of the sensed biological reference signal; and
determining an optimal multiplication vector x, such that a product of the convolution matrix H and the optimal multiplication vector x produce a solution vector b', where the solution vector b' is a solution that is most closely correlated to the sensed cardiac source signal.

9. The method of claim 1, further comprising reducing redundancy in the sensed biological reference signal.

10. The method of claim 9, wherein reducing the redundancy in the sensed biological reference signal comprises performing principal component analysis on the sensed biological reference signal.

11. The method of claim 1, further comprising identifying beat timings in the sensed biological reference signal.

12. The method of claim 11, further comprising: identifying beat windows around the identified beat timings in the sensed biological reference signal and the sensed cardiac source signal; and concatenating the beat windows to produce a concatenated sensed biological reference signal and a concatenated sensed cardiac source signal.

13. A catheter system for mapping a chamber of a heart, the system comprising:
a plurality of electrodes configured to sense a first set of one or more activation signals in the chamber of the heart, wherein each of the activation signals of the first set comprises a near-field signal component and a far-field signal component;
one or more electrodes configured to sense a second set of one or more activation signals, wherein the second set of activation signals are representative of the far-field signal components of the first set of activation signals; and
a processor configured to receive the sensed first set of one or more activation signals and the sensed second set of one or more second activation signals, wherein the processor is configured to: process the second set of activation signals; generate, based at least in part on the processed second set of activation signals, an estimated far-field signal component for each activation signal in the first set of activation signals; and subtract the estimated far-field signal components from the corresponding first activation signals.

14. The system of claim 13, wherein to generate, based at least in part on the processed second set of activation signals, an estimated far-field signal component for each activation signal in the first set of activation signals, the processor is configured to: generate one or more shifted copies of the processed second set of activation signals; project the one or more shifted copies onto each of the activation signals of the first set of activation signals.

15. The system of claim 14, wherein projecting the one or more shifted copies onto each of the activation signals of the first set of activation signals produces the estimated far-field signal component for each activation signal in the first set of activation signals, wherein the estimated far-field signal components are the estimated far-field signal components that are most closely correlated to the far-field signal components of the activation signals in the first set of activation signals.

16. The system of claim 15, wherein projecting comprises performing one or more techniques comprised of: least-squares regression; constrained least-squares; maximum likelihood estimation; non-linear programming; and linear programming.

17. The system of claim 13, wherein to process the second set of activation signals, the processor is configured to: produce one or more concatenated beat window signals from the one or more second activation signals.

18. A method for reducing a ventricular signal artifact in a sensed atrial signal, the method comprising:
sensing one or more ventricular signals with a plurality of electrodes;
sensing an atrial signal using a plurality of electrodes, wherein the atrial signal comprises an atrial signal component and an artifact signal component that is representative of the one or more ventricular signals;
generating one or more shifted copies of the one or more ventricular signals;
estimating, based at least in part on the generated one or more shifted copies of the one or more ventricular signals, the artifact signal component; and
filtering the artifact signal component from the atrial signal.

19. The method of claim 18, wherein filtering the artifact signal component comprises: subtracting the estimated artifact signal component from the atrial signal.

20. The method of claim 18, wherein estimating, based at least in part on the generated one or more shifted copies of the one or more ventricular signals, the artifact signal component comprises projecting the estimating one or more shifted copies of the one or more ventricular signals onto the atrial signal.

* * * * *